(12) United States Patent
Javanmard et al.

(10) Patent No.: US 11,604,133 B2
(45) Date of Patent: Mar. 14, 2023

(54) USE OF MULTI-FREQUENCY IMPEDANCE CYTOMETRY IN CONJUNCTION WITH MACHINE LEARNING FOR CLASSIFICATION OF BIOLOGICAL PARTICLES

(71) Applicant: Rutgers, The State University of New Jersey, New Brunswick, NJ (US)

(72) Inventors: Mehdi Javanmard, West Windsor, NJ (US); Karan Ahuja, Bluffdale, UT (US); Jianye Sui, Piscataway, NJ (US); Joseph R. Bertino, Branford, CT (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 281 days.

(21) Appl. No.: 16/851,580

(22) Filed: Apr. 17, 2020

(65) Prior Publication Data

US 2020/0333235 A1 Oct. 22, 2020

Related U.S. Application Data

(60) Provisional application No. 62/836,838, filed on Apr. 22, 2019.

(51) Int. Cl.
| | | |
|---|---|---|
| G06K 9/00 | (2022.01) | |
| G01N 15/10 | (2006.01) | |
| G01N 33/50 | (2006.01) | |
| G06N 5/04 | (2023.01) | |
| G06N 20/00 | (2019.01) | |

(52) U.S. Cl.
CPC ..... G01N 15/1031 (2013.01); G01N 33/5005 (2013.01); G06N 5/04 (2013.01); G06N 20/00 (2019.01); *G01N 2015/1006* (2013.01)

(58) Field of Classification Search
CPC ....... G01N 2015/1006; G01N 15/1031; G01N 2800/7028; G01N 33/5005
See application file for complete search history.

(56) References Cited

U.S. PATENT DOCUMENTS

| | | | | |
|---|---|---|---|---|
| 9,625,472 | B2* | 4/2017 | Xu | G01N 33/5005 |
| 9,683,253 | B2* | 6/2017 | Liu | B03C 5/026 |
| 10,690,677 | B2* | 6/2020 | Xu | C12M 25/08 |
| 2007/0172939 | A1* | 7/2007 | Xu | C12M 41/36 |
| | | | | 435/287.1 |
| 2012/0127473 | A1* | 5/2012 | Pfaff | G01B 11/164 |
| | | | | 356/457 |
| 2012/0287431 | A1* | 11/2012 | Matsiev | G01N 27/026 |
| | | | | 356/306 |
| 2014/0284221 | A1* | 9/2014 | Liu | G01N 15/1031 |
| | | | | 204/403.01 |
| 2016/0195479 | A1* | 7/2016 | Pfaff | G01N 21/23 |
| | | | | 356/458 |
| 2017/0048467 | A1* | 2/2017 | Chuang | H04N 5/335 |
| 2017/0322137 | A1* | 11/2017 | Feher | G01N 15/1429 |
| 2018/0333724 | A1* | 11/2018 | Hull | G01N 15/0266 |
| 2022/0120698 | A1* | 4/2022 | Norman | G06T 7/0004 |

\* cited by examiner

*Primary Examiner* — Hadi Akhavannik
(74) *Attorney, Agent, or Firm* — Fox Rothschild LLP

(57) ABSTRACT

This disclosure provides methods and systems for classifying biological particles, e.g., blood cells, microbes, circulating tumor cells (CTCs). Using impedance flow cytometry, such as multi-frequency impedance cytometry, in conjunction with supervised machine learning, the disclosed methods and systems demonstrated improved accuracy in classifying biological particles.

15 Claims, 13 Drawing Sheets

| Classifier | Accuracy to classify between blood cells and cancer cells. |
|---|---|
| *Logistic Regression* | 99.5% |
| *K Nearest Neighbors* | 99.2% |
| *Support Vector Machine* | 98.6% |

FIG. 9

USE OF MULTI-FREQUENCY IMPEDANCE CYTOMETRY IN CONJUNCTION WITH MACHINE LEARNING FOR CLASSIFICATION OF BIOLOGICAL PARTICLES

CROSS-REFERENCE TO RELATED APPLICATIONS

This application claims priority under 35 U.S.C. § 119(e) to U.S. Provisional Patent Application No. 62/836,838, filed Apr. 22, 2019. The foregoing application is incorporated by reference herein in its entirety.

STATEMENT REGARDING FEDERALLY SPONSORED RESEARCH

This invention was made with government support under Grant Number 1556253 awarded by the National Science Foundation and under Contract Number 75A50119C00048 from the Department of Health and Human Services, Office of the Assistant Secretary for Preparedness and Response, and Biomedical Advanced Research and Development Authority, DRIVe. This invention was also made with government support under Grant Number 1846740 from the National Science Foundation, under Grant Number NNX16AO69A from the Translational Research Institute through NASA, and under the PhRMA Foundation Research Starter Grants awarded to Mehdi Javanmard. The government has certain rights in the invention.

FIELD OF THE INVENTION

This disclosure relates generally to methods and systems for classifying biological particles and more specifically to methods and systems for classifying biological particles using multi-frequency impedance cytometry in conjunction with machine learning.

BACKGROUND OF THE INVENTION

Circulating cancer cells (CTCs) refer to a small fraction of cells in patient blood resembling the cells of the primary tumor (Ashworth, T., Aust Med J., 1869. 14: p. 146). These cells circulate in the bloodstream after being shed from the tumor site. CTCs belong to a class of extremely rare cells (as low as 1 in $10^9$ erythrocytes and 1 in $10^7$ leukocytes) which makes detection and analysis of CTCs challenging (Baccelli, I.n., et al., Nature Biotechnology, 2013. 31(6): p. 539; Viraka Nellore, B. P., et al., Bioconjugate chemistry, 2015. 26(2): p. 235-242.). CTCs have been found in the majority of epithelial cancers, including those from colon, breast, lung, and prostate. Although CTCs are rare in quantity, the analysis of CTCs is extraordinarily promising. They serve as a prognostic marker and likely to be the precursor for the formation of secondary tumors during metastasis. In addition, CTC analysis provides insight into treatment effectiveness and can facilitate the discovery of biomarkers to monitor treatment response.

With rapid advances in oncology, microfluidics, and medicine, CTC detection, isolation, and characterization technologies have shown promising results and have attracted more attention. The most commonly used method for CTC isolation relies on antibody-based capture of CTCs. CTCs express epithelial cell surface markers that are absent from normal leukocytes. The VERIDEX CELLSEARCH system (NJ, USA) is a commercially available system approved by FDA that uses cell surface antigen, an epithelial cell adhesion molecule (EpCAM), to identify target cells (e.g., CTCs). However, this system is not widely used because the system is expensive and suffers from low sensitivity and selectivity. In addition, the purity of captured CTCs is very low (Xiong, K., et al., Advanced Materials, 2016. 28(36): p. 7929-7935.). Nagrath et al. developed a unique microfluidic CTC chip that utilizes an array of microposts which are functionalized with anti-EpCAM antibodies which allowed longitudinal monitoring of patients during therapy and molecular characterization of CTCs (Nagrath, S., et al., Nature, 2007. 450(7173): p. 1235.). In addition to CTCs, the ability to classify and quantify different types of blood cells can be used as biomarkers for various chronic and acute conditions. This includes red blood cells, platelets, and white blood cells with differentials. Quantification of white blood cell differentials (e.g., Neutrophils, monocytes, and lymphocytes) can provide information as to whether an infection is viral or bacterial and also can be useful for risk stratification of sepsis patients and COVID19 infected patients. Physical properties to distinguish CTCs from blood have been vastly explored. These properties include cell size, shape, charge, deformability, and density. Filtration, hydrodynamic chromatography, dielectrophoresis, and inertial microfluidics have shown promising results and avoid the use of cell surface antigens.

A key challenge in utilizing physical properties of CTCs is that the inherent heterogeneity of CTCs causes a significant overlap of physical properties with leukocytes. This results in leukocyte contamination in the output sample. Thus, there remains a strong need for methods and systems capable of detecting or classifying biological particles, such as CTCs.

SUMMARY OF THE INVENTION

This disclosure addresses the need mentioned above in a number of aspects. In one aspect, this disclosure provides a system for classifying biological particles, comprising: a non-transitory, computer-readable memory; one or more processors; and a computer-readable medium containing programming instructions that, when executed by the one or more processors, cause the system to: (i) measure an impedance response of one or more biological particles in a sample at one or more frequencies to generate impedance response data associated with the one or more biological particles in the sample; (ii) determine physical properties of the generated impedance response data at the one or more frequencies; and (iii) classify the one or more biological particles in the sample into categories based on the determined physical properties of the generated impedance response data at the one or more frequencies by applying a machine learning model to the generated impedance response data.

In another aspect, this disclosure also provides a system for determining a type of a biological particle, comprising: a non-transitory, computer-readable memory; one or more processors; and a computer-readable medium containing programming instructions that, when executed by the one or more processors, cause the system to: (a) measure an impedance response of a biological particle in a sample at one or more frequencies using multi-frequency impedance cytometry to generate impedance response data associated with the biological particle in the sample; (b) determine physical properties of the generated impedance response data at the one or more frequencies; and (c) determine a type of the biological particle in the sample based on the determined physical properties of the generated impedance response data at the one or more frequencies by applying a machine learning model to the generated impedance response data.

In yet another aspect, this disclosure further provides a method of classifying biological particles, comprising: (i) measuring an impedance response of one or more biological particles in a sample at one or more frequencies to generate impedance response data associated with the one or more biological particles in the sample; (ii) determining physical properties of the generated impedance response data at the one or more frequencies; and (iii) classifying the one or more biological particles in the sample into categories based on the determined physical properties of the generated impedance response data at the one or more frequencies by applying a machine learning model to the generated impedance response data.

In yet another aspect, this disclosure additionally provides a method of determining a type of a biological particle, comprising: (a) measuring an impedance response of a biological particle in a sample at one or more frequencies using multi-frequency impedance cytometry to generate impedance response data associated with the biological particle in the sample; (b) determining physical properties of the generated impedance response data at the one or more frequencies; and (c) determining a type of the biological particle in the sample based on the determined physical properties of the generated impedance response data at the one or more frequencies by applying a machine learning model to the generated impedance response data.

In another aspect, this disclosure also provides a method of diagnosing a patient as having a cancer or suspected of having a cancer characterized by the presence of circulating cancer cells (CTCs) in a sample from the patient, comprising: (i) obtaining from the patient a sample comprising one or more biological particles; (ii) measuring an impedance response of the one or more biological particles in the sample at one or more frequencies using multi-frequency impedance cytometry to generate impedance response data associated with the one or more biological particles in the sample; (iii) determining physical properties of the generated impedance response data at the one or more frequencies; and (iv) determining the presence of a CTC in the one or more biological particles based on the determined physical properties of the generated impedance response data at the one or more frequencies by applying a machine learning model to the generated impedance response data.

In some embodiments, the step of measuring the impedance response is performed using multi-frequency impedance cytometry. In some embodiments, the one or more frequencies comprise a frequency of between about 100 Hz and about 30 MHz.

In some embodiments, the determined physical properties of the generated impedance response data comprise electrical properties. In some embodiments, the electrical properties comprise amplitude of the impedance response, phase of the impedance response, or both.

In some embodiments, the machine learning model comprises Support Vector Machine, K Nearest Neighbors, Logistic Regression, Random Forests, Deep Learning, or other AI techniques.

In some embodiments, the biological particles comprise cells. In some embodiments, the cells comprise white blood cells, red blood cells, or cancer cells. In some embodiments, the cancer cells comprise CTCs.

In some embodiments, the step of determining the physical properties of the generated impedance response data comprises detrending and denoising the generated impedance response data.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 4B is a normalized amplitude response of blood cells at 500 KHz, 300 KHz, and 1 MHz. Each peak corresponds to a single cell passing by.

FIG. 9 illustrates a comparison in different machine learning classifiers to classify between blood cells and cancer cells.

DETAILED DESCRIPTION OF THE INVENTION

Figure 1:
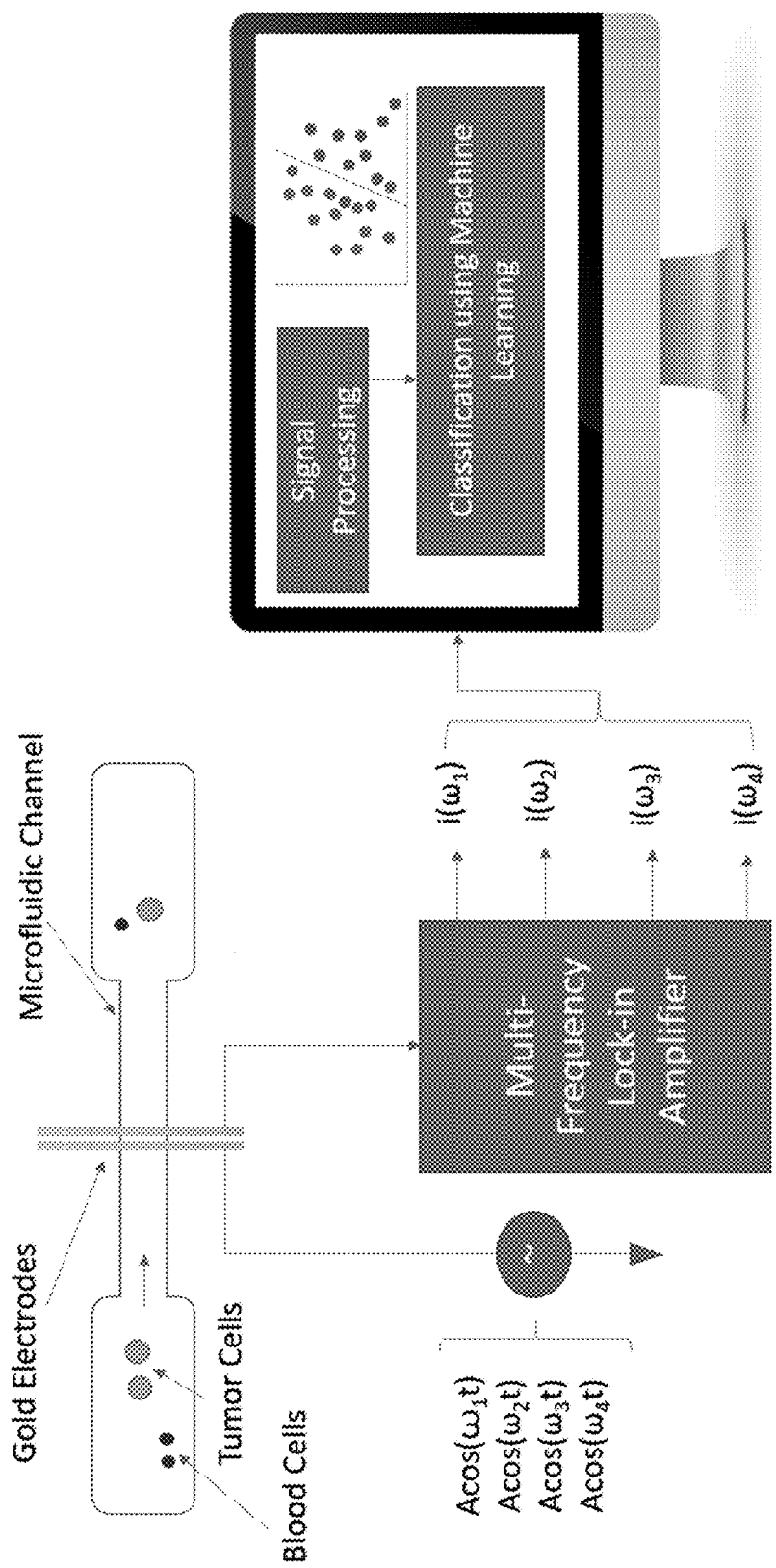
FIG. 1 is a schematic diagram of an example system for classifying cells. Multi-frequency impedance cytometry measures the impedance response of cancer cells and blood across a broad range of frequencies.

This disclosure provides methods and systems for classifying biological particles, e.g., circulating tumor cells (CTCs) using impedance flow cytometry, such as multi-frequency impedance cytometry. The classification of biological particles can be performed in conjunction with one or more machine learning models (e.g., supervised machine learning). Multi-frequency impedance cytometry allows screening of biological particles based on their dielectric properties. This disclosure demonstrated rapid differentiation of cancer cells from blood cells using multi-frequency impedance cytometry and supervised machine learning for enhanced classification and accuracy.

A. Methods and Systems for Classifying Biological Particles

In one aspect, this disclosure provides a system for classifying biological particles (e.g., CTCs), comprising: a non-transitory, computer-readable memory; one or more processors; and a computer-readable medium containing programming instructions that, when executed by the one or more processors, cause the system to: (i) measure an impedance response of one or more biological particles in a sample at one or more frequencies to generate impedance response data associated with the one or more biological particles in the sample; (ii) determine physical properties of the generated impedance response data at the one or more frequencies; and (iii) classify the one or more biological particles in the sample into categories based on the determined physical properties of the generated impedance response data at the one or more frequencies by applying a machine learning model to the generated impedance response data.

In another aspect, this disclosure also provides a system for determining a type of a biological particle (e.g., CTC), comprising: a non-transitory, computer-readable memory; one or more processors; and a computer-readable medium containing programming instructions that, when executed by the one or more processors, cause the system to: (a) measure an impedance response of a biological particle in a sample at one or more frequencies using multi-frequency impedance cytometry to generate impedance response data associated with the biological particle in the sample; (b) determine physical properties of the generated impedance response data at the one or more frequencies; and (c) determine a type of the biological particle in the sample based on the determined physical properties of the generated impedance response data at the one or more frequencies by applying a machine learning model to the generated impedance response data.

The biological particle(s) may be from the living being. The biological particle(s) can be a cell, a bacterium, a virus, a protein, a microparticle, a nanoparticle, a nucleic acid, a biomarker, or a bead with a biological material attached thereto. In some embodiments, the particle can be any microbial cellular organism (e.g., bacteria, archaea, fungi, protozoa, algae, and viruses). In some embodiments, the biological particles comprise CTCs.

The cell, according to this embodiment, may be collected from any kind of multicellular organisms. Specific examples of the cell include somatic cells collected from mammals (e.g., a human, a mouse, a monkey, a pig, a rat), and cells obtained by culturing cells isolated from each mammal or each mammalian cell line. Examples of the somatic cells include: keratinous epithelial cells (e.g., keratinocytes); mucosal epithelial cells (e.g., tongue epithelial cells); exocrine epithelial cells (e.g., mammary glandular cells); hormone-secreting cells (e.g., adrenomedullary cells); metabolic and storage cells (e.g., hepatocytes); interface-forming luminal epithelial cells (e.g., type I alveolar cells); vascular luminal epithelial cells (e.g., vascular endothelial cells); ciliated cells with transport function (e.g., tracheal epithelial cells); extracellular matrix secretory cells (e.g., fibroblasts); contractile cells (e.g., smooth muscle cells); hematopoietic and immune cells (e.g., T cells); sensory cells (e.g., rod cells); automatic nervous system neurons (e.g., cholinergic neurons); sensory and peripheral neuron-supporting cells (e.g., satellite cells); CNS neurons and glial cells (e.g., astrocytes); pigment cells (e.g., retinal pigment epithelial cells); and progenitors (tissue precursors) thereof. The cell differentiation degree and/or how old an animal, a source of the cell, is are not particularly limited. An undifferentiated progenitor (including a somatic stem cell) or a fully differentiated mature cell may be likewise used as a source of a somatic cell of the present invention. As used herein, examples of the undifferentiated progenitor include tissue stem cells (somatic stem cells) such as neural stem cells, hematopoietic stem cells, mesenchymal stem cells, and dental pulp stem cells. Preferable examples of an individual mammal, which is a source of the somatic cell according to the present invention, include, but are not particularly limited to, humans. In addition, more preferred are cells artificially processed after the somatic cells have been sampled. Examples include induced pluripotent stem cells (iPS cells) prepared from the somatic cells and cells obtained after pluripotent stem cells (e.g., ES cells and iPS cells) have been differentiated.

In some embodiments, the step of measuring the impedance response is performed using multi-frequency impedance cytometry. In some embodiments, the one or more frequencies comprise a frequency of between about 100 Hz and about 30 MHz (e.g., between about 100 Hz and about 3 MHz, between about 300 KHz and about 30 MHz, between about 100 Hz and about 300 KHz, between about 300 KHz and about 3 MHz, between about 3 MHz and about 30 MHz).

In some embodiments, the determined physical properties of the generated impedance response data comprise electrical properties. In some embodiments, the electrical properties comprise amplitude of the impedance response, phase of the impedance response, or both.

In some embodiments, the machine learning model comprises Support Vector Machine, K Nearest Neighbors, or Logistic Regression. For example, the method using a machine learning model may include training one or more machine learning classifiers on the generated impedance response data. In some embodiments, the method may include one or more machine learning classifiers comprising any of Support Vector Machine, K Nearest Neighbors, and Logistic Regression, Random Forests, Deep Learning, or other AI techniques.

In some embodiments, the step of determining the physical properties of the generated impedance response data comprises detrending and denoising the generated impedance response data.

In some embodiments, the biological particles comprise cells. In some embodiments, the cells comprise white blood cells, red blood cells, or cancer cells (e.g., CTCs). In some embodiments, the biological particles can be provided in a bodily fluid (e.g., blood) or a buffer solution.

Cancers may comprise non-solid tumors (such as hematologic tumors, e.g., leukemias and lymphomas) or may comprise solid tumors, which may include carcinoma, blastoma and sarcoma, and certain leukemias or malignant lymphoid tumors, benign and malignant tumors and malignancies, e.g., sarcomas, carcinomas, and melanomas. Also included are adult tumors/cancers and pediatric tumors/ cancers. Hematologic cancers are cancers of the blood or bone marrow. Examples of hematologic (or hematogenous) cancers include leukemias, including acute leukemias (such as acute lymphocytic leukemia, acute myelocytic leukemia, acute myelogenous leukemia, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high-grade forms), myeloma Multiple, Waldenstrom's macroglobulinemia, heavy chain disease, myelodysplastic syndrome, hairy cell leukemia, and myelodysplasia.

In some embodiments, the cancer is selected from the group consisting of oral cancer, oropharyngeal cancer, nasopharyngeal cancer, respiratory cancer, urogenital cancer, gastrointestinal cancer, central or peripheral nervous system tissue cancer, an endocrine or neuroendocrine cancer or hematopoietic cancer, glioma, sarcoma, carcinoma, lymphoma, melanoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer, and skin cancer.

CTCs originated from primary tumors play critical roles in metastasis. CTCs shed into the circulation allow a window of opportunity for early diagnosis of cancer. In one aspect, this disclosure relates to the use of multi-frequency impedance cytometry and machine learning to classify CTCs and normal blood cells for early diagnosis of cancer. For example, the method can be used to differentiate T47D breast cancer cells and blood samples.

Electrical properties of CTCs can help delve further in the isolation, detection, and analysis of CTCs. Tumor cell characterization and classification using impedance spectroscopy recorded significant differences in cytoplasm conductivity and cell membrane for paired high-metastatic and low metastatic cells. Here the measurements were performed over a frequency range from 100 Hz to 3 MHz. Impedance spectrum of cells >3 MHz can also lead to valuable insights regarding cell viability, membrane properties, and shape.

Multi-frequency impedance cytometry allows screening of biological cells based on their dielectric properties. With rapid advances in machine learning, algorithms can enable computers to access hidden insights from data, and thus it has emerged as an important tool in the field of biology and medicine. In this disclosure, it was demonstrated that the disclosed methods could rapidly distinguish cancer cells from blood cells using multi-frequency impedance cytometry and supervised machine learning for enhanced classification and accuracy. The electrical properties (e.g., phase and amplitude) of cancer cells and blood were also compared, which help accurately quantify and analyze circulating tumor cells from blood in patients.

Compared to the existing methods for CTC detection, such as tissue biopsy, antibody-based detection, molecular diagnostics based on circulating tumor DNA, the method of the present invention has at least the following advantages: (1) it is label-free and thus cost-effective, as compared to several existing methods that require immunolabeling of surface antigens; and (2) in comparison with existing CTC detection platforms, there would be a significant reduction of the size and cost of the readout instrument. It can also be implemented as point-of-care applications.

In yet another aspect, this disclosure further provides a method of classifying biological particles, comprising: (i) measuring an impedance response of one or more biological particles in a sample at one or more frequencies to generate impedance response data associated with the one or more biological particles in the sample; (ii) determining physical properties of the generated impedance response data at the one or more frequencies; and (iii) classifying the one or more biological particles in the sample into categories based on the determined physical properties of the generated impedance response data at the one or more frequencies by applying a machine learning model to the generated impedance response data.

In yet another aspect, this disclosure additionally provides a method of determining a type of a biological particle, comprising: (a) measuring an impedance response of a biological particle in a sample at one or more frequencies using multi-frequency impedance cytometry to generate impedance response data associated with the biological particle in the sample; (b) determining physical properties of the generated impedance response data at the one or more frequencies; and (c) determining a type of the biological particle in the sample based on the determined physical properties of the generated impedance response data at the one or more frequencies by applying a machine learning model to the generated impedance response data.

In another aspect, this disclosure also provides a method of diagnosing a patient as having a cancer or suspected of having a cancer characterized by the presence CTCs in a sample from the patient, comprising: (i) obtaining from the patient a sample comprising one or more biological particles; (ii) measuring an impedance response of the one or more biological particles in the sample at one or more frequencies using multi-frequency impedance cytometry to generate impedance response data associated with the one or more biological particles in the sample; (iii) determining physical properties of the generated impedance response data at the one or more frequencies; and (iv) determining the presence of a CTC in the one or more biological particles based on the determined physical properties of the generated impedance response data at the one or more frequencies by applying a machine learning model to the generated impedance response data.

FIG. 1 is a block diagram showing an example system for classifying or detecting biological particles. The system may include a microfluidic channel embedded on a fused silica wafer with gold electrodes (FIG. 2), a multi-frequency lock-in amplifier (ZURICH INSTRUMENTS), and software to record and analyze the data. As an example, impedance cytometry experiments with T47D cancer cells and human blood cells were conducted. After the cells were cultured, T47D cells in the media (RPMI 1640) were centrifuged (290 G for 5 minutes) and suspended in 1×PBS (~400 cells/µL) to perform the impedance cytometry experiments. Blood cells were also suspended in 1×PBS, and the concentration was ~400 cells/µL.

The impedance cytometry measurements were conducted at discrete frequencies ranging from 300 KHz to 30 MHz. For each cell type, a series of measurements were performed at four discrete frequencies simultaneously. A frequency of 500 KHz was used as one of the frequencies for each set of measurements.

Figure 3:
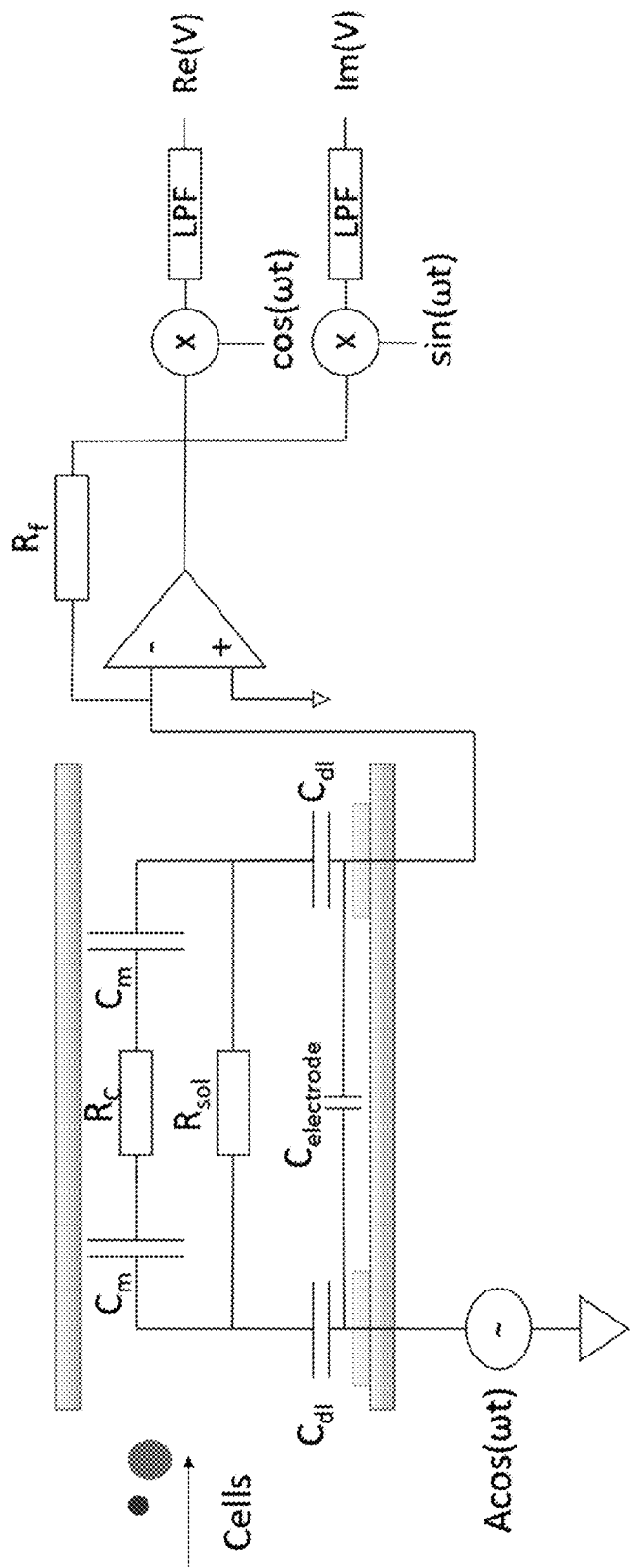
FIG. 3 illustrates an equivalent circuit model of the electrode-electrolyte interface in the microchannel along with the readout circuit for measuring changes in resistance across the channel.
Figure 4A:
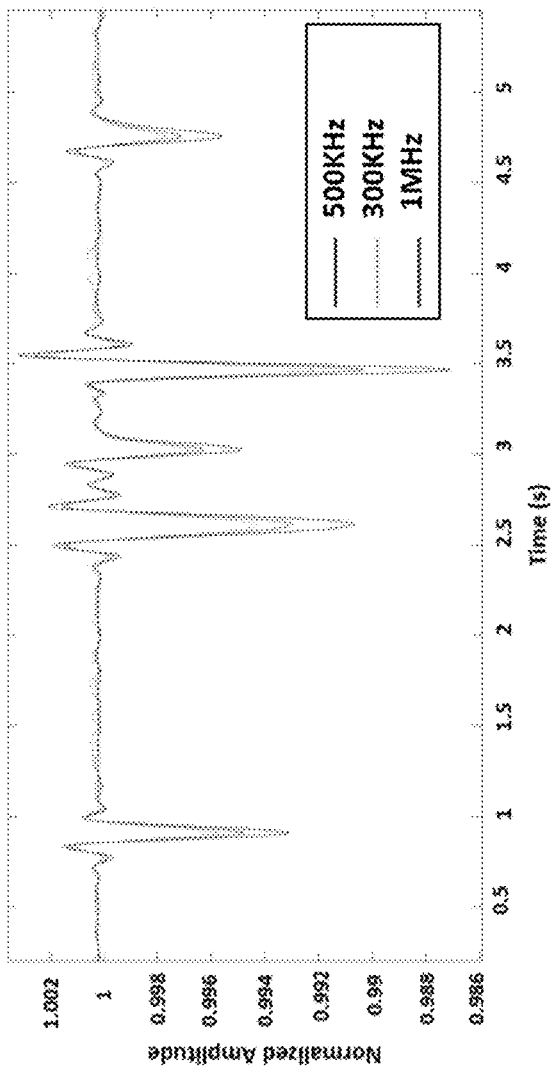
FIG. 4A illustrates a normalized amplitude response of live cancer cells at 500 KHz, 300 KHz, and 1 MHz.
Figure 4B:
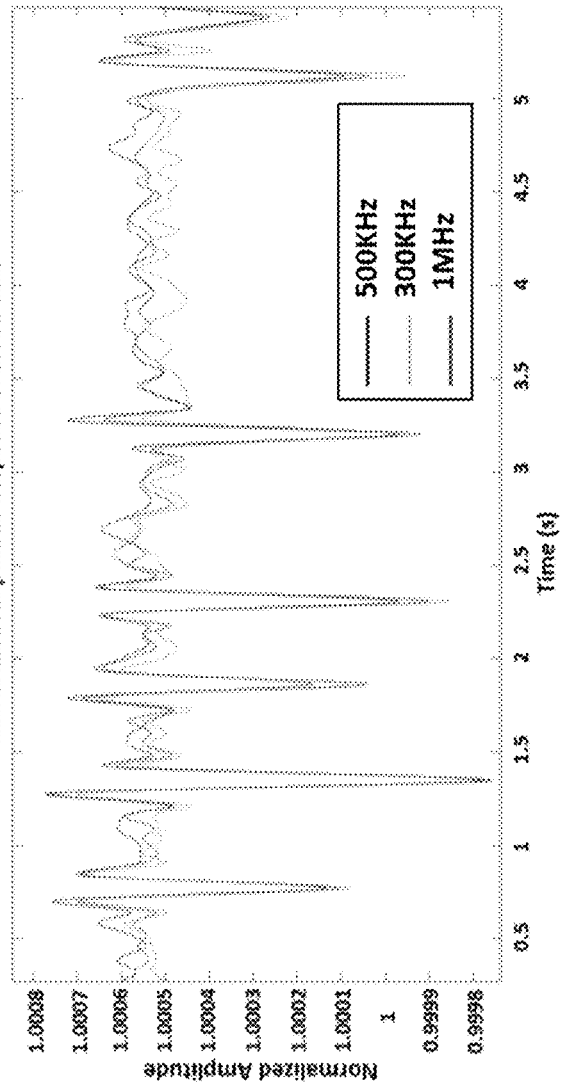

In one example, an ideal polarizable electrode system with no faradic reactions was assumed as gold was the electrode material. A double layer of ions with opposing polarity is formed when an AC voltage is applied across the two electrodes, which is commonly referred to as double-layer capacitance. A simplified circuit model with a double layer capacitance ($C_{dl}$) at each electrode in series with the solution resistance ($R_s$) in parallel with the coupling capacitance between two electrodes in the cell ($C_{cell}$) is shown in FIG. 3. Passage of cells through the pore results in modulation of ionic resistance. FIG. 4 represents the normalized response of T47D cancer cells and blood at different frequencies. Each peak corresponds to a single cell being detected. The measurements were performed using a lock-in amplifier and software to record the data.

The recorded data was then post processed in MATLAB using an algorithm to detrend and denoise the data. This helped the analysis of the impedance cytometry data with minimal error. After detrending and denoising the data, two significant features were extracted from the data: amplitude change and phase change. Amplitude change was termed as a change in amplitude level when a cell passes by, which implies the difference between the baseline voltage and the voltage when a cell passes by. In other words, amplitude change is determined as:

$$\text{Amplitude Change} = \sqrt{\text{Re}(V)^2 + \text{Im}(V)^2}\bigg|_{cell\ passing\ by} - \sqrt{\text{Re}(V)^2 + \text{Im}(V)^2}\bigg|_{baseline} \quad (1)$$

Figures 5A, 5B:
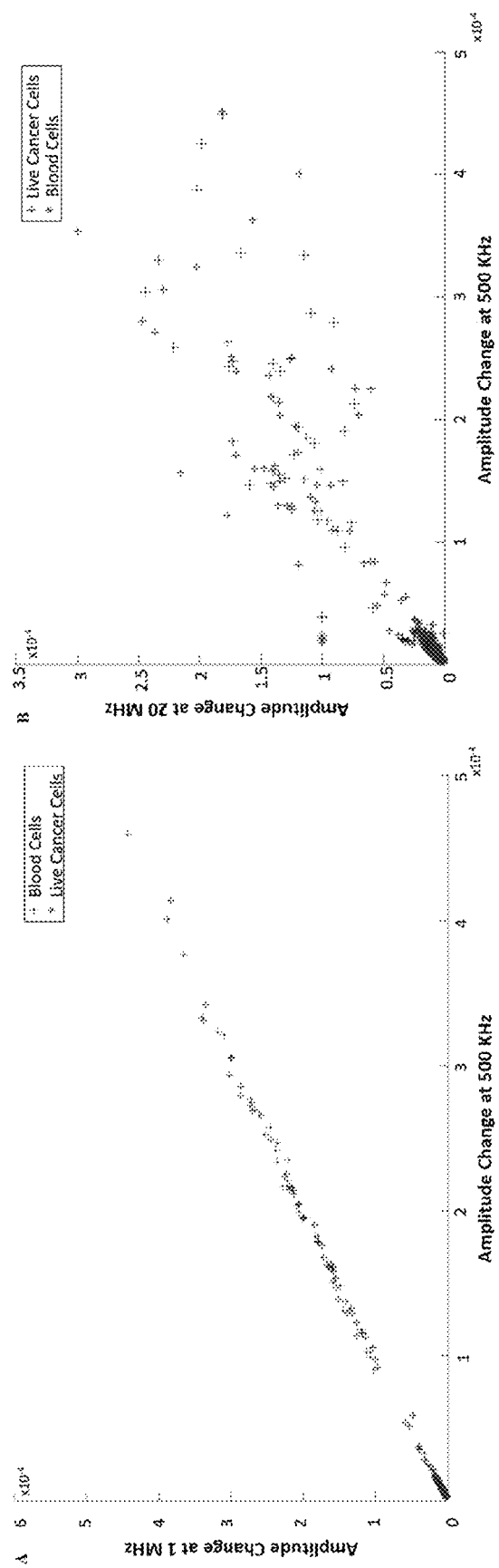
FIGS. 5A and 5B are the scatter plots showing amplitude change for live cancer cells and blood at different frequencies.

This change in amplitude was calculated for each single cell passing by with respect to its baseline for all the frequencies at which measurements were conducted. FIG. 5A presents a scatter plot of amplitude change for T47D cancer cells (live) and blood cells at 500 KHz and 1 MHz and FIG. 5B presents scatter plot of amplitude change for T47D cancer cells and blood cells at 500 KHz and 20 MHz Phase change was termed as the change in angular position of the excitation frequency when a cell passes by. This was calculated from the real and imaginary data points obtained from the data. A phase change is determined as:

$$\text{Phase Change} = \tan^{-1}\left(\frac{\text{Im}(V)}{\text{Re}(V)}\right)_{cell\ passig\ by} - \tan^{-1}\left(\frac{\text{Im}(V)}{\text{Re}(V)}\right)_{baseline} \quad (2)$$

Figures 6A, 6B:
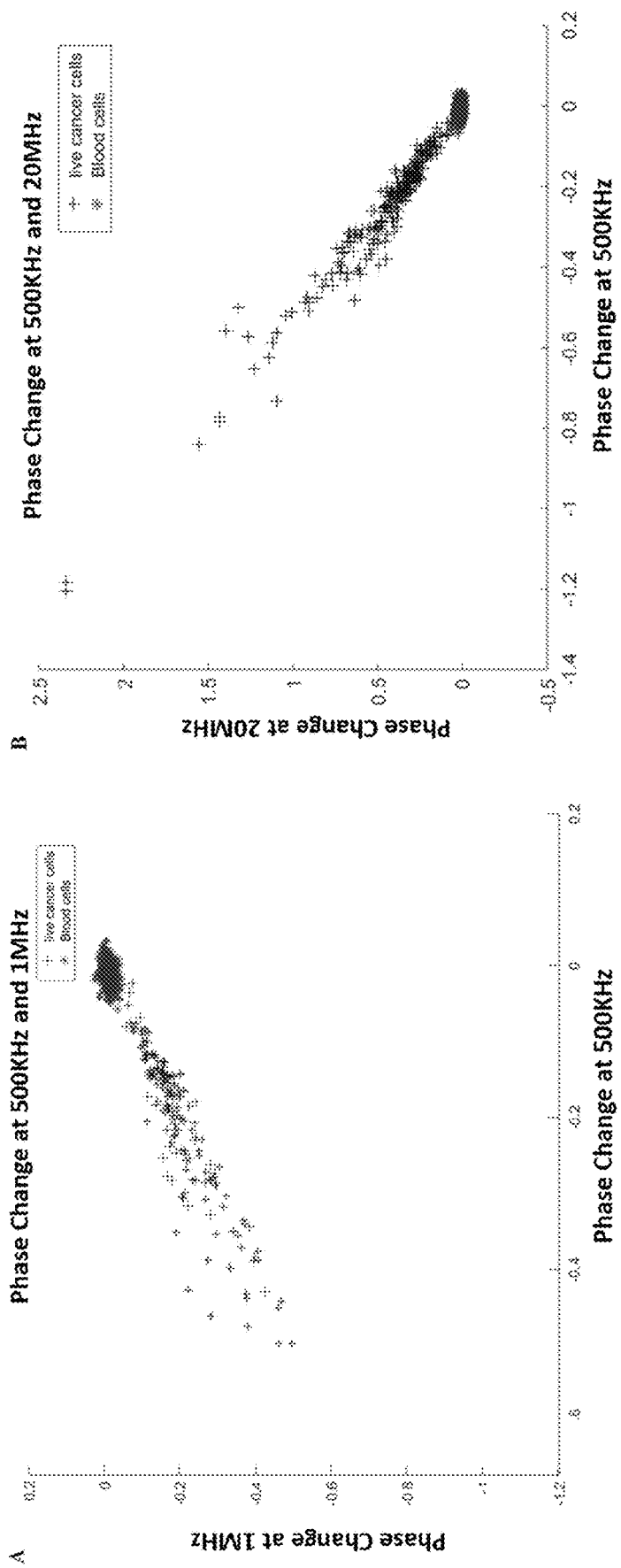
FIGS. 6A and 6B are the scatter plots showing phase change for live cancer cells and blood at different frequencies.

Again, change in phase was calculated for each single cell passing by for all the frequencies at which measurements were conducted. FIG. 6A presents a scatter plot of phase change for T47D cancer cells (Live) and blood cells at 500 KHz and 1 MHz and FIG. 6B presents a scatter plot of phase change for T47D cancer cells and blood cells at 500 KHz and 20 MHz.

Machine Learning Analysis

Figure 7:
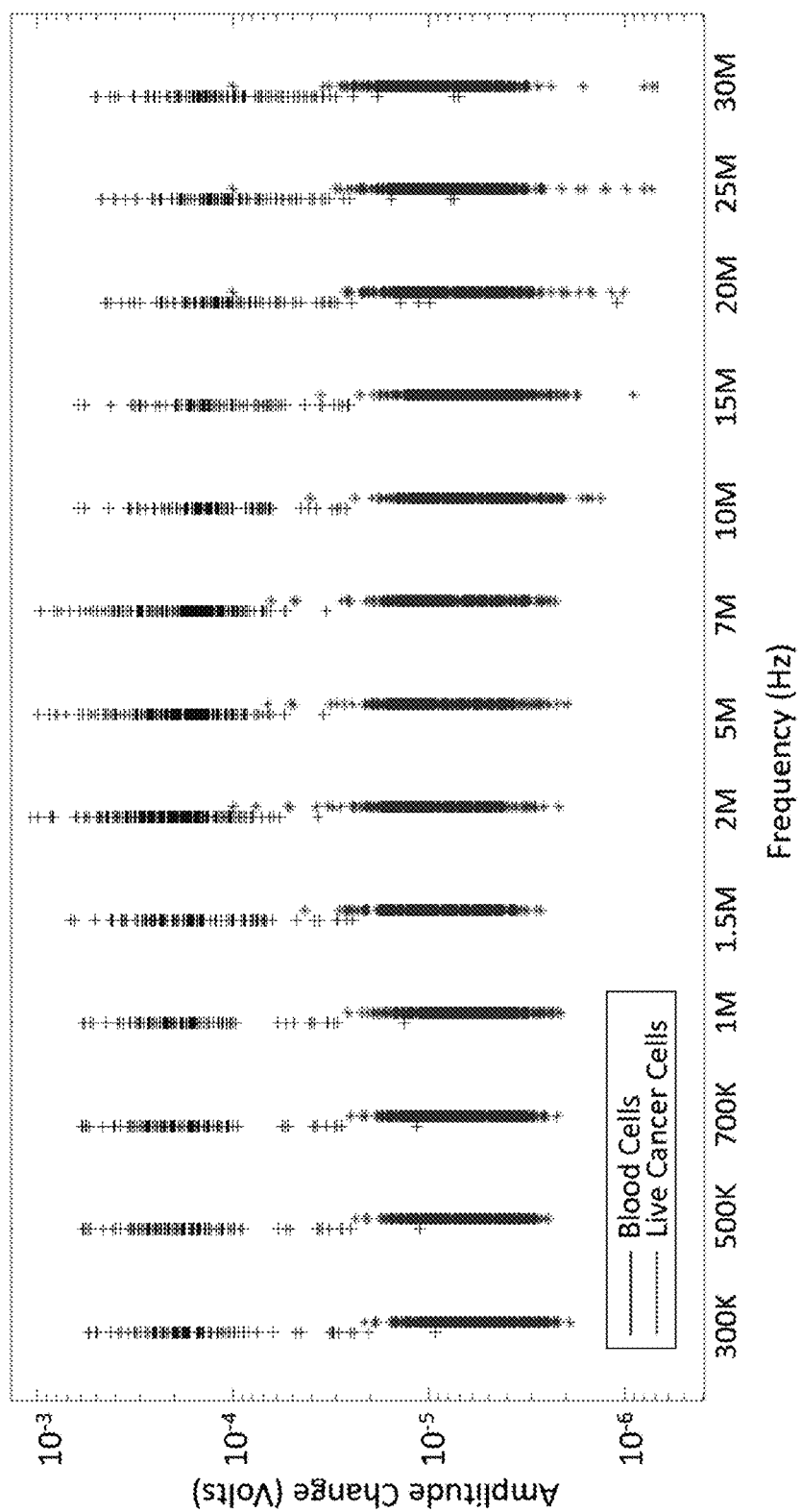
FIG. 7 illustrates an amplitude spectrum of live cancer cells and blood.
Figure 8:
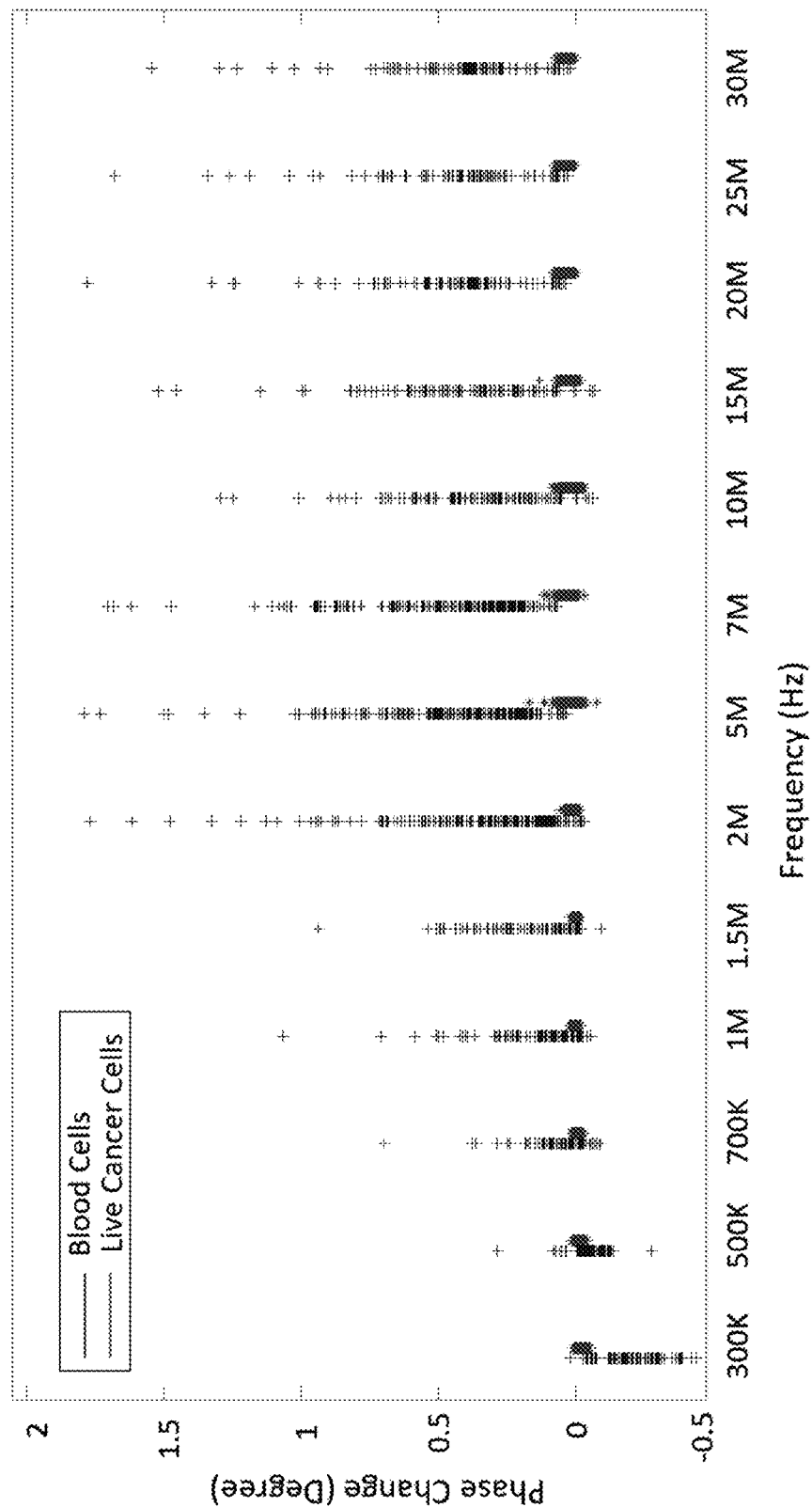
FIG. 8 illustrates a phase spectrum of live cancer cells and blood.

Although cancer cells differ in size from white blood cells and red blood cells, classifying or comparing them based on size alone might not be accurate/efficient in some conditions. Classifying cells based on their dielectric/internal properties and size can help achieve high accuracy. Higher frequencies (>10 MHz) tend to probe the internal properties of the cell. FIG. 7 presents the amplitude spectrum of T47D cancer cells and blood cells, and FIG. 8 presents the phase spectrum of T47D cancer cells and blood cells. For phase change, a general trend was observed, wherein the change (in phase) was negative at lower frequencies (2 MHz) and positive at higher frequencies. In other words, a frequency-dependent impedance change may differ based upon the type of cell that exists (e.g., red blood cell versus cancer cell).

To apply a machine learning model for analyzing impedance response data, the Classification Learner Toolbox in MATLAB was used to analyze the impedance cytometry data. The toolbox contains several machine learning classifiers like Support Vector Machine, K Nearest Neighbors, Logistic Regression etc., which can be readily trained on the data set. Next, how accurately these algorithms can classify between cancer cells and blood was tested. A feature matrix consisting of phase change data at 500 KHz, 20 MHz, 25 MHz, and 30 MHz and amplitude change data at 500 KHz, 20 MHz, 25 MHz, and 30 MHz was constructed to train the classifier. The feature matrix was normalized to ensure all the data points lie within the same range. The feature matrix consisted of more than 1000 data points for training to ensure the classifiers did not face the problem of overfitting.

The machine learning model may be trained using various datasets to perform specific pattern recognition. For example, the algorithms for detecting amplitude and/or phase of the impedance response may be trained using the impedance response data at various frequencies obtained from multi-frequency impedance cytometry. The machine learning model may employ any one of the following algorithms, including, without limitation, support vector machines (SVMs), neural network, logistic regression, naive Bayes, memory-based learning, random forests, bagged trees, decision trees, boosted trees, boosted stumps, etc. Some embodiments of the machine learning module use unsupervised machine learning that provides training data without labeled responses. Examples of unsupervised machine learning techniques use clustering, for example, k-means clustering, hierarchical clustering, and so on.

For example, neural network technology, also known as "artificial neural network (ANN)," is one of the most developed tools used in machine learning modules for pattern recognition. Neural networks are constructed of processing elements known as neurons. Neurons are interconnected and arranged in a plurality of layers. Each neuron can have multiple inputs but generally only one output, which, in turn, is usually connected to many or all other neurons in the next layer. Neural networks learn by extracting relational information from the data and the desired output. A neural network in the machine learning module is initially trained or fed large amounts of data. Data reflecting amplitude and/or phase of the impedance response at one or more frequencies of individual types of biological particles can be fed to the neural network during the training stage. After the training stage, the resulting neural network is capable of determining the type of individual biological particle, thus enabling the system to classify biological particles based on their physical properties, such as electrical properties. In some embodiments, the machine learning module may employ a plurality of neural networks, which may be organized either in series, in parallel, or in a nested fashion. In this example, the neural networks are arranged in a tree pattern or in a hierarchical structure, with each neural network trained to perform a particular pattern recognition task. A group of such neural networks may be coupled to other groups of neural networks to handle more complex tasks.

FIG. 9 represents the accuracy of different machine learning classifiers to classify between cancer cells and blood cells. Logistic regression reported to have the highest classification accuracy (99.5%). Logistic regression is a discriminative classifier that works by extracting weighted features from input (data), taking logarithms, and then combining them linearly. K Nearest Neighbors reported classification accuracy of 99.2% and Support Vector Machine (SVM) reported to have a classification accuracy of 98.6%, among others.

Figure 12A:
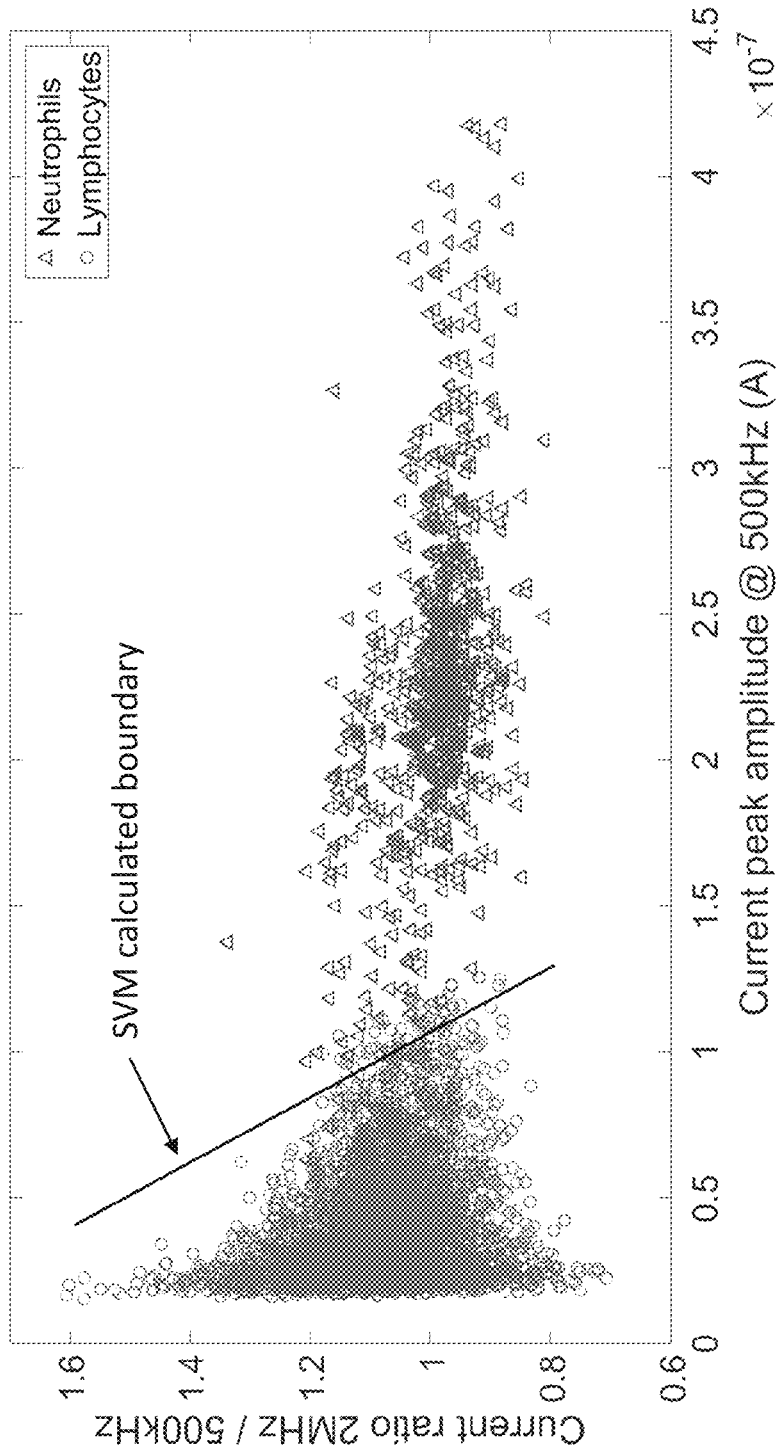
FIGS. 12A, 12B, and 12C are a set of graphs showing classification of white blood cell subtypes, such as neutrophils and lymphocytes, using the disclosed methods.
Figure 12C:
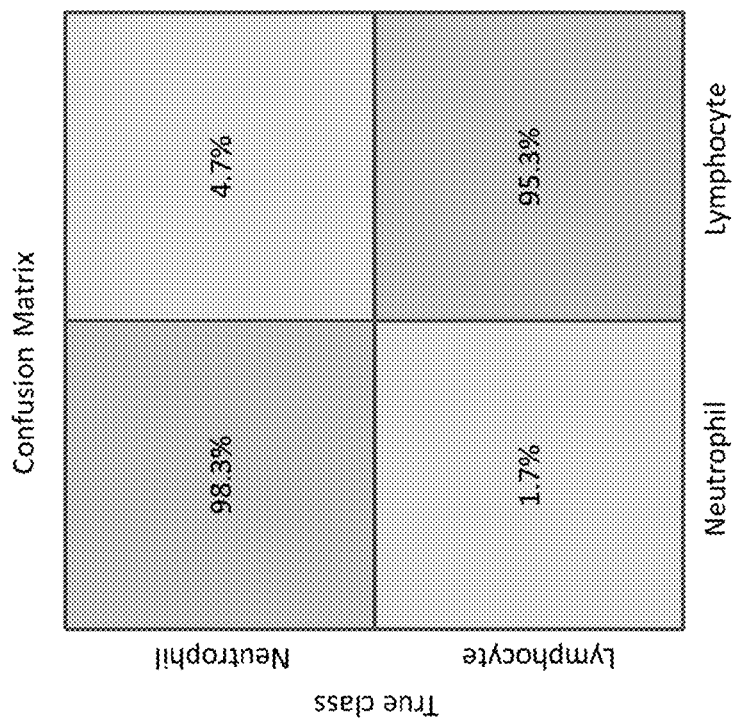
Figure 12B:
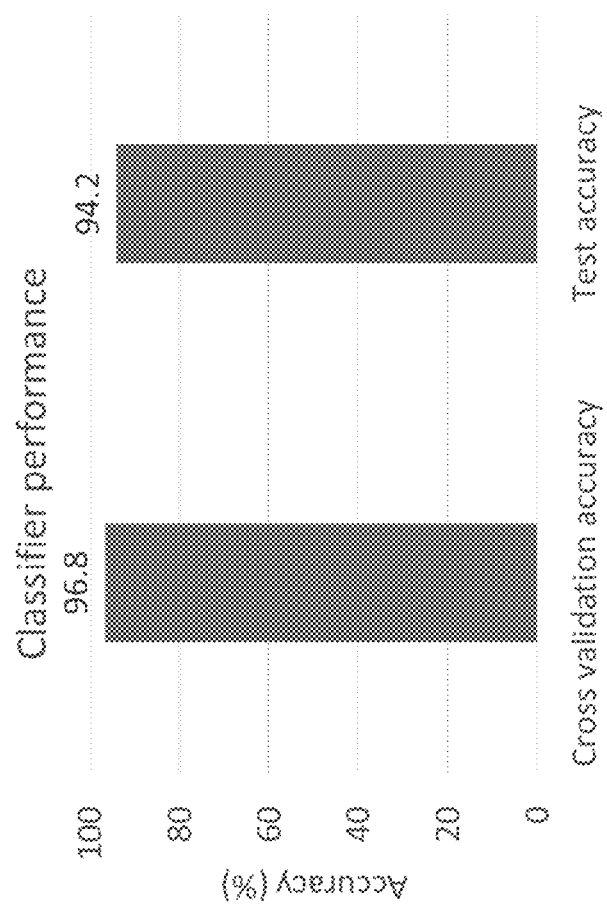

FIGS. 12A, 12B, and 12C are a set of graphs showing classification of white blood cell sub-types, namely neutrophils and lymphocytes, using the disclosed methods. A SVM classifier was trained using purified neutrophils and purified lymphocytes and tested on mixed samples. The classifier was trained with labeled data described by many features, whereby the classifier determines the optimal boundary for accurately classifying the data. The accuracy of the classifier is then assessed using test data with known values.

FIG. 12A is a scatter plot showing responses of neutrophils and lymphocytes in terms of output current. The data are collected at two different frequencies, 500 KHz and 2 MHz, using impedance flow cytometry. Each current peak signals a cell flowing through the cytometer. The x-axis shows the current peak amplitude measured at 500 KHz and the y-axis shows the ratio of current peak amplitude at 2 MHz to the current peak amplitude at 500 KHz. The current peak at 500 KHz is affected primarily by cell diameter, while the current peak at 2 MHz is a product of the cells internal properties such as membrane thickness and cytoplasm conductivity and dielectric constant. The ratio of these two amplitudes provides a parameter that is independent of cell size, reflecting changes in the cell properties.

FIG. 12B is a scatter plot showing the amplitudes of the two cell types at the two frequencies. Two distinct clusters clearly appear in this scatter plot. Neutrophils are larger in size than lymphocytes and as a result, and they exhibited larger peak amplitude at 500 KHz. The neutrophil and lymphocyte are separated by the solid black line, and the classification boundary determined by the SVM algorithm.

The performance of SVM in classifying neutrophils and lymphocytes is depicted in FIGS. 12B and 12C. FIG. 12B shows 10-fold cross validation accuracy and test accuracy of the SVM classifier and both of them are above 90%. As the confusion matrix illustrates in FIG. 12C, few cells are misclassified using SVM classifier. The false positive rate and false negative rate are within 5%. These results demonstrate that using the SVM algorithm along with impedance flow cytometry, it is possible to accurately differentiate between neutrophils and lymphocytes.

Electrode Fabrication

Electrodes on glass wafer were fabricated using standard photolithography on a 3" fused silica wafer. The process involved photo-patterning resist on a fused silica wafer, electron beam metal evaporation, and liftoff processing. The process of photo-patterning included wafer cleaning, spin coating the photoresist, soft bake of the resist, ultraviolet light exposure through a chromium mask printed on a 4"×4" glass plate, resist development and hard bake of the resist. After the photo-patterning process, a 100 nm gold layer was deposited on the substrate using electron beam evaporation. A 10 nm layer of chromium was used to enhance the adhesion of gold to the glass wafer; otherwise, the gold film gets peeled off easily. Gold was chosen as the electrode due to its resistance to corrosion and inert nature. The width of the electrodes was 20 µm, and the spacing between the two electrodes was 25 µm.

Microfluidic Channel Fabrication

Figure 2A:
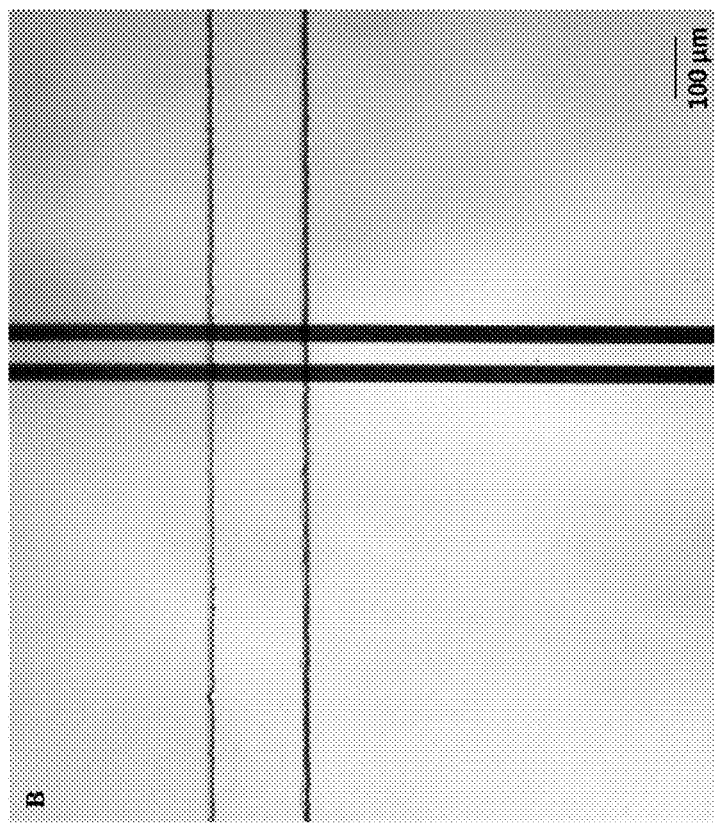
FIG. 2A illustrates microfabricated electrodes at the channel.
Figure 2B:
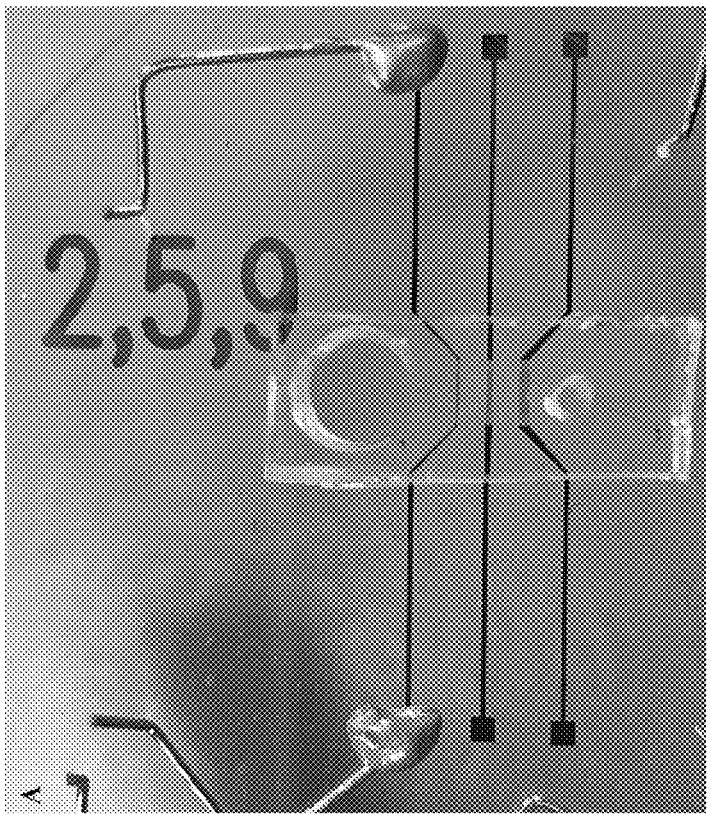
FIG. 2B is an image of a PDMS device bonded to the electrode.

The microfluidic channel itself was fabricated in PDMS (Poly-dimethylsiloxane) by using soft lithography. A layer of SU-8 was patterned onto a 3" Silicon wafer that acts as a master mold. The SU-8 photo-patterning process involves standard cleaning, spin coating, soft baking, ultraviolet light exposure through a chromium mask, development, and hard baking. After the master mold was fabricated, PDMS (10:1 pre-polymer/curing agent) was poured onto the master mold and baked at 80° C. for over two hours for curing. The PDMS channel was then peeled off from the mold. A 5 mm hole and a 1.5 mm hole were then punched to form the inlet and outlet, respectively. The PDMS substrate was aligned and bonded it to the electrode chip after both substrates have undergone oxygen plasma treatment. The bonded chip was then baked at 70° C. for 30 minutes to form an irreversible bond. The microfluidic channel had a width of 100 µm and a height of 30 µm. FIG. 2A represents microfabricated electrodes bonded with the channel, and the image of PDMS device bonded to electrodes is shown in FIG. 2B.

Cell Culture

T47D breast cancer cell line (in American Tissue Culture Collection, also known as HB-133) is a luminal type-A breast cancer cell line obtained from a pleural effusion from a ductal breast cancer carcinoma patient. The cell line is also classified according to the expression of the receptors for hormonal therapy and thus classified as ER+(means estrogen receptor-positive), PR+(progesterone receptor-positive), and HER2− (Herceptin receptor 2 negative). For cell culture, RPMI 1640 media, and Fetal bovine serum albumin from Invitrogen (Fischer Scientific) were used. Cell viability was determined using the Vi-CEL Series Cell Viability Analyzer (Beckman Coulter, Carlsbad, Calif.). The viability was close to 100%.

Computer System and Network

Figure 10:
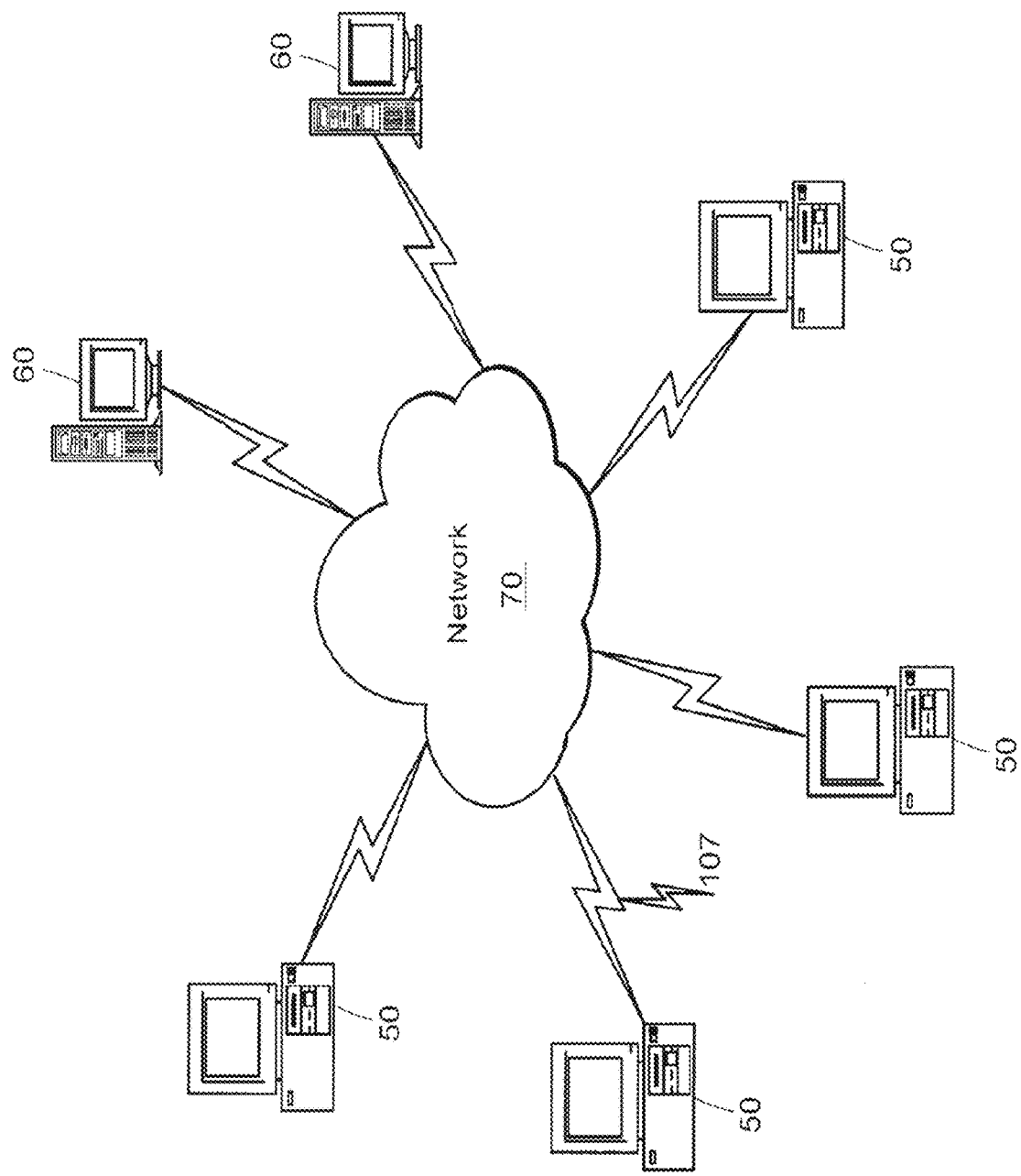
FIG. 10 is a schematic view of a computer network system or similar digital processing environment.

FIG. 10 illustrates a computer network (and system) or similar digital processing environment, according to some embodiments 1000. Client computer(s)/devices 50 and server computer(s) 60 provide processing, storage, and input/output devices executing application programs and the like. The client computer(s)/devices 50 can also be linked through communications network 70 to other computing devices, including other client devices/processes 50 and server computer(s) 60. The communications network 70 can be part of a remote access network, a global network (e.g., the Internet), a worldwide collection of computers, local area or wide area networks, and gateways that currently use respective protocols (TCP/IP, Bluetooth®, etc.) to communicate with one another. Other electronic device/computer network architectures are suitable.

Client computers/devices 50 may be configured with a computing module. Server computers 60 may be configured with a data module which communicates with client devices (i.e., computing modules) 50 for improving computer security (including but not limited to user data protection) of a device using machine learning. The server computers 60 may not be separate server computers but part of cloud network 70. In some embodiments, the server computer (e.g., display module) may enable users to improve computer security (including but not limited to user data protection) of a device using machine learning-based techniques (described herein) that may be located on the client 50, server 60, or network 70 (e.g., global computer network). The client (computing module) 50 may communicate information regarding the system back to and/or from the server 60 (data module). In some embodiments, the client 50 may include client applications or components (e.g., computing module) executing on the client 50 for generating or receiving (or accessing) data, and the client 50 may communicate this information to the server (e.g., data module) 60.

In other words, according to some embodiments, the computer system of FIG. 10 may include a data module 60 configured to automatically measure the impedance response of the one or more biological particles. The data module 60 may further be configured to store the generated impedance response data. The computing module 50 may be operatively coupled to the data module 60. The computing module 50 may be configured to analyze the physical properties of the generated impedance response data.

Figure 11:
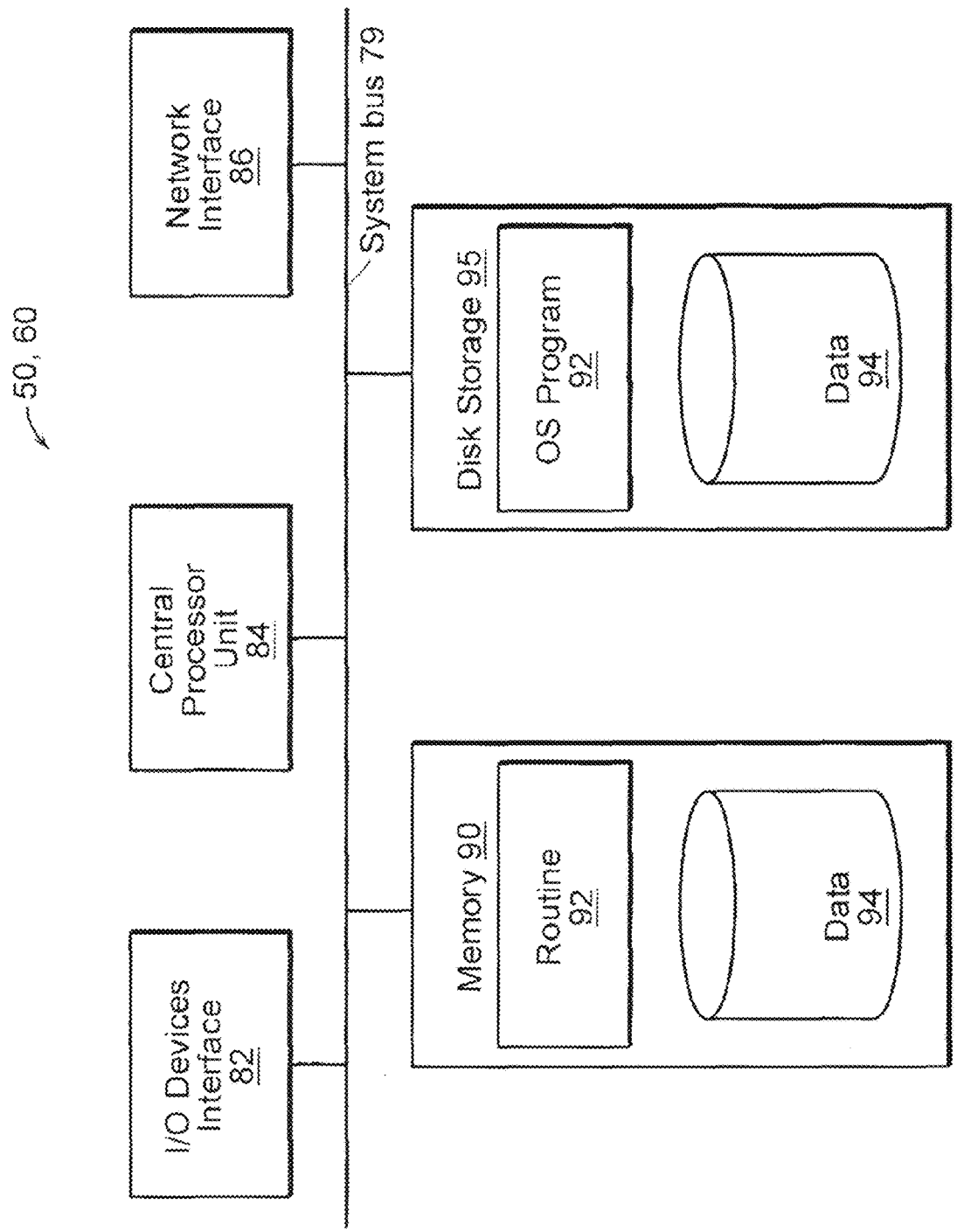
FIG. 11 is a block diagram of an example internal structure of a computer processing device (e.g., client processor/device or server computers) in the computer network system of FIG. 10.

According to some embodiments, FIG. 11 is a diagram of an example internal structure of a computer (e.g., client processor/device 50 or server computers 60) in the computer system of FIG. 10. Each computer 50, 60 contains a system bus 79, where a bus is a set of hardware lines used for data transfer among the components of a computer or processing system. The system bus 79 is essentially a shared conduit that connects different elements of a computer system (e.g., processor, disk storage, memory, input/output ports, network ports, etc.) that enables the transfer of information between the elements. Attached to the system bus 79 is an I/O device interface 82 for connecting various input and output devices (e.g., keyboard, mouse, displays, printers, speakers, etc.) to the computer 50, 60. A network interface 86 allows the computer to connect to various other devices attached to a network (e.g., network 70 of FIG. 10). Memory 90 provides volatile storage for computer software instructions 92 and data 94 used to implement some embodiments 1000 (e.g., data module, computing module, and/or display module engine elements described herein). Disk storage 95 provides non-volatile storage for computer software instructions 92 and data 94 used to implement an embodiment of the present disclosure. A central processor unit 84 is also attached to the system bus 79 and provides for the execution of computer instructions.

In one embodiment, the processor routines 92 and data 94 are a computer program product (generally referenced 92), including a computer-readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network (s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer-readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium, and the like.

Embodiments 1000 or aspects thereof may be implemented in the form of hardware (including but not limited to hardware circuitry), firmware, or software. If implemented in software, the software may be stored on any non-transient computer-readable medium that is configured to enable a processor to load the software or subsets of instructions thereof. The processor then executes the instructions and is configured to operate or cause an apparatus to operate in a manner as described herein.

Further, hardware, firmware, software, routines, or instructions may be described herein as performing certain actions and/or functions of the data processors. However, it should be appreciated that such descriptions contained herein are merely for convenience and that such actions, in fact, result from computing devices, processors, controllers, or other devices executing the firmware, software, routines, instructions, etc.

It should be understood that the flow diagrams, block diagrams, and network diagrams may include more or fewer elements, be arranged differently, or be represented differently. But it further should be understood that certain implementations may dictate the block and network diagrams and the number of block and network diagrams illustrating the execution of the embodiments be implemented in a particular way.

Accordingly, further embodiments may also be implemented in a variety of computer architectures, physical, virtual, cloud computers including but not limited to both single-tenant and multi-tenant systems, and/or some combination thereof, and, thus, the data processors described herein are intended for purposes of illustration only and not as a limitation of the embodiments.

This disclosure presents a novel microfluidic device to analyze impedance cytometry data by using phase and amplitude properties for both cancer cells and blood. The heterogeneity between cancer cells and blood allows us to rapidly measure their properties. The platform technology, as disclosed herein, can be used to accurately quantify and analyze circulating tumor cells from blood in patients. Real tumor cells, however, will exhibit more heterogeneity compared to cultured cancer cells. However, separation consisting of both phase and magnitude rather than size alone can yield more accurate results.

B. Definitions

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

As used herein, the terms "subject," "patient," or "living being" are used interchangeably irrespective of whether the subject has or is currently undergoing any form of treatment. As used herein, the terms "subject" and "subjects" may refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgus monkey, chimpanzee, etc.) and a human). The subject may be a human or a non-human. In this context, a "normal," "control," or "reference" subject, patient, or population is/are one(s) that exhibit(s) no detectable disease or disorder, respectively.

"Sample," "test sample," and "patient sample" may be used interchangeably herein. The sample can be a sample of serum, urine plasma, amniotic fluid, cerebrospinal fluid, cells (e.g., antibody-producing cells) or tissue. Such a sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. The terms "sample" and "biological sample" as used herein generally refer to a biological material being tested for and/or suspected of containing an analyte of interest such as antibodies. The sample may be any tissue sample from the subject. The sample may comprise protein from the subject.

Any cell type, tissue, or bodily fluid may be utilized to obtain a sample. Such cell types, tissues, and fluid may include sections of tissues such as biopsy and autopsy samples, frozen sections taken for histologic purposes, blood (such as whole blood), plasma, serum, sputum, stool, tears, mucus, saliva, hair, skin, red blood cells, platelets, interstitial fluid, ocular lens fluid, cerebral spinal fluid, sweat, nasal fluid, synovial fluid, menses, amniotic fluid, semen, etc. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose). Archival tissues, such as those having treatment or outcome history, may also be used. Protein purification may not be necessary.

Methods well known in the art for collecting, handling and processing urine, blood, serum, and plasma, and other body fluids, can be used in the practice of the present disclosure, for instance, when the antibodies provided herein are employed as immunodiagnostic reagents, and/or in an immunoassay kit. The test sample can comprise further moieties in addition to the analyte of interest, such as antibodies, antigens, haptens, hormones, drugs, enzymes, receptors, proteins, peptides, polypeptides, oligonucleotides or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary, pretreatment optionally can be done for mere convenience (e.g., as part of a regimen on a commercial platform). The sample may be used directly as obtained from the subject or following a pretreatment to modify a characteristic of the sample. Pretreatment may include extraction, concentration, inactivation of interfering components, and/or the addition of reagents.

The terms "determining," "measuring," "assessing," and "assaying" are used interchangeably and include both quantitative and qualitative measurement, and include determining if a characteristic, trait, or feature is present or not. Assessing may be relative or absolute. "Assessing the presence of" a target includes determining the amount of the target present, as well as determining whether it is present or absent.

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of the presence or absence of the disease or condition. Each factor or symptom that is considered to be indicative of the diagnosis of a particular disease does not need to be exclusively related to the particular disease; i.e., there may be differential diagnoses that can be inferred from a diagnostic factor or symptom. Likewise, there may be instances where a factor or symptom that is indicative of a particular disease is present in an individual that does not have a particular disease. The diagnostic methods may be used independently or in combination with other diagnosing and/or staging methods known in the medical art for a particular disease or disorder.

The term "prognosis" as used herein refers to a prediction of the probable course and outcome of a clinical condition or disease. Prognosis is usually made by evaluating factors or symptoms of a disease that are indicative of a favorable or unfavorable course or outcome of the disease. The phrase "determining the prognosis" as used herein refers to the process by which the skilled artisan can predict the course or outcome of a condition in a patient. The term "prognosis" does not refer to the ability to predict the course or outcome of a condition with 100% accuracy instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

It is noted here that, as used in this specification and the appended claims, the singular forms "a," "an," and "the" include plural reference unless the context clearly dictates otherwise.

The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

The word "substantially" does not exclude "completely," e.g., a composition which is "substantially free" from Y may be completely free from Y. Where necessary, the word "substantially" may be omitted from the definition of the invention.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise. In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates, which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A system for classifying biological particles, comprising:
    a non-transitory, computer-readable memory;
    one or more processors; and
    a computer-readable medium containing programming instructions that, when executed by the one or more processors, cause the system to:
    measure an impedance response of one or more biological particles in a sample at multiple frequencies simultaneously and using a multi-frequency lock-in amplifier to generate impedance response data associated with the one or more biological particles in the sample, wherein the multiple frequencies are from 100 kHz to 10 MHz;
    determine physical properties of the generated impedance response data at the multiple frequencies, wherein the determined physical properties of the generated impedance response data comprise electrical properties that comprise amplitude of the impedance response, phase of the impedance response, or both; and
    classify the one or more biological particles in the sample into categories based on the determined physical properties of the generated impedance response data at the multiple frequencies by applying a machine learning model trained with measurements of the multi-frequency lock-in amplifier and amplitudes of the impedance response at the multiple frequencies to the generated impedance response data.

2. The system of claim 1, wherein the step of measuring the impedance response is performed using multi-frequency impedance cytometry.

3. The system of claim 1, wherein the machine learning model comprises Support Vector Machine, K Nearest Neighbors, Logistic Regression, Random Forests, or Deep Learning.

4. The system of claim 1, wherein the biological particles comprise cells.

5. The system of claim 4, wherein the cells comprise white blood cells, red blood cells, or cancer cells.

6. The system of claim 5, wherein the cancer cells comprise circulating cancer cells (CTCs).

7. The system of claim 1, wherein the step of determining the physical properties of the generated impedance response data comprises detrending and denoising the generated impedance response data.

8. A system for determining a type of a biological particle, comprising:
    a non-transitory, computer-readable memory;
    one or more processors; and
    a computer-readable medium containing programming instructions that, when executed by the one or more processors, cause the system to:
    measure an impedance response of a biological particle in a sample at multiple frequencies simultaneously using multi-frequency impedance cytometry and a multi-frequency amplifier to generate impedance response data associated with the biological particle in the sample, wherein the multiple frequencies are from 100 kHz to 10 MHz;
    determine physical properties of the generated impedance response data at the multiple frequencies, wherein the determined physical properties of the generated impedance response data comprise electrical properties that comprise amplitude of the impedance response, phase of the impedance response, or both; and
    determine a type of the biological particle in the sample based on the determined physical properties of the generated impedance response data at the multiple frequencies by applying a machine learning model trained with measurements of the multifrequency lock-in amplifier and amplitudes of the impedance response at the multiple frequencies to the generated impedance response data.

9. A method of classifying biological particles, comprising:
  measuring an impedance response of one or more biological particles in a sample at multiple frequencies simultaneously and using a multi-frequency lock-in amplifier to generate impedance response data associated with the one or more biological particles in the sample, wherein the multiple frequencies are from 100 kHz to 10 MHz;
  determining physical properties of the generated impedance response data at the multiple frequencies, wherein the determined physical properties of the generated impedance response data comprise electrical properties that comprise amplitude of the impedance response, phase of the impedance response, or both; and
  classifying the one or more biological particles in the sample into categories based on the determined physical properties of the generated impedance response data at the multiple frequencies by applying a machine learning model trained with measurements of the multi-frequency lock-in amplifier and amplitudes of the impedance response at the multiple frequencies to the generated impedance response data.

10. The method of claim 9, wherein the step of measuring further comprises measuring the impedance response using multi-frequency impedance cytometry.

11. The method of claim 9, wherein the machine learning model comprises Support Vector Machine, K Nearest Neighbors, Logistic Regression, Random Forests, or Deep Learning.

12. The method of claim 9, wherein the biological particles comprise cells.

13. The method of claim 12, wherein the cells comprise white blood cells, red blood cells, or cancer cells.

14. The method of claim 13, wherein the cancer cells comprise circulating cancer cells (CTCs).

15. The method of claim 9, wherein the step of determining the physical properties of the generated impedance response data comprises detrending and denoising the generated impedance response data.

* * * * *